United States Patent [19]

Mitsuya et al.

[11] Patent Number: 5,616,566

[45] Date of Patent: *Apr. 1, 1997

[54] METHOD OF INHIBITING HIV REPLICATION WITH 2',3'-DIDEOXYADENOSINE

[75] Inventors: Hiroaki Mitsuya, Rockville; Samuel Broder; Robert Yarchoan, both of Bethesda, all of Md.

[73] Assignee: The United States of America as represented by the Department of Health and Human Services, Washington, D.C.

[ * ] Notice: The term of this patent shall not extend beyond the expiration date of Pat. No. 5,254,539.

[21] Appl. No.: 56,043

[22] Filed: Apr. 30, 1993

Related U.S. Application Data

[62] Division of Ser. No. 663,288, Feb. 28, 1991, Pat. No. 5,254,539, which is a continuation of Ser. No. 420,664, Aug. 28, 1989, abandoned, which is a continuation of Ser. No. 84,055, Aug. 11, 1987, Pat. No. 4,861,759, which is a continuation-in-part of Ser. No. 937,925, Dec. 4, 1986, abandoned, which is a continuation-in-part of Ser. No. 769,016, Aug. 26, 1985, abandoned.

[51] Int. Cl.$^6$ .................. A61K 31/70; C07H 19/173; C07H 19/20
[52] U.S. Cl. .............. 514/47; 514/46; 536/26.26; 536/27.6
[58] Field of Search .................. 514/46, 47, 48; 536/27.14, 26.26, 27.6

[56] References Cited

U.S. PATENT DOCUMENTS

| | | | |
|---|---|---|---|
| 3,817,982 | 6/1974 | Verheyden et al. | 536/27.14 |
| 4,081,534 | 3/1978 | Elion et al. | 514/46 |
| 4,434,788 | 3/1984 | Nakatsugawa | 514/45 |
| 4,481,197 | 11/1984 | Rideout et al. | 514/46 |
| 4,577,012 | 3/1986 | Tsurushima et al. | 536/26.73 |
| 4,861,759 | 8/1989 | Mitsuya et al. | 514/43 |
| 4,920,210 | 4/1990 | Koszalka et al. | 536/27.14 |
| 5,026,687 | 10/1993 | Yarchoan et al. | 514/45 |
| 5,254,539 | 10/1993 | Mitsuya et al. | 514/46 |

OTHER PUBLICATIONS

Cheng et al., 1987, "Human Immunodeficiency Virus Reverse Transcriptase," J. Biol. Chem. 262 (No. 5): 2187–2189.

Mitsuya et al., Oct. 1985, "3'-Azido-3'-Deoxythymidine (BW A509U): An Antiviral Agent That Inhibits The Infectivity And Cytopathic Effect Of Human T–Lymphotropic Virus Type III/Lymphadenopathy–Associated Virus *In Vitro*", Proc. Natl. Acad. Sci. USA 82: 7096–7100.

Mitsuya et al., 1986, "Inhibition Of The *In Vitro* Infectivity And Cytopathic Effect Of Human T–Lymphotrophic Virus Type III/Lymphadenopathy–Associated Virus (HTLV–III/LAV) By 2',3'-Dideoxynucleosides," Proc. Natl. Acad. Sci. USA 83: 1911–1915.

Furmanski et al., 1980, Inhibition by 2',3'-Dideoxythymidine of Retroviral Infection of Mouse and Human Cells. Cancer Letters, 8:307–315.

Ho et al., 1985, Recombinant Human Interferon Alfa–A Supresses HTLV–III Replication In Vitro. Lancet i:602–604.

Martin et al., 1987, Synthesis and Antiviral Activity of Various Esters of 9–[(1,3–Dihydroxy–2–propoxy)methyl] guanine. J. Pharmaceutical Sciences, 76(2):180–184.

McCormick et al., 1984, Ribavirin Suppresses Replication of Lymphadenopathy–Associated Virus in Cultures of Human Adult T–lymphocytes, Lancet ii:1367–1369.

Mitsuya et al., 1984, Suramin Protection of T Cells in Vitro Against Infectivity and Cytopathic Effect of HTLV–III. Science, 226:172–174.

Mitsuya et al., 1985, Protection of T Cells Against Infectivity and Cytopathic Effect of HTLV–III In Vitro. Retroviruses in Human Lymphoma/Leukemia, M. Miwa et al. (Eds.), Japan Sci. Soc. press., 277–288.

Mitsuya et al., 1987, Rapid In Vitro Systems For Assessing Activity of Agents Against HTLV–III/LAV. Ch. 18 AIDS: Modern Concepts and Therapeutic Changes, Broder (Eds.), 303–333.

Prisbe et al., 1985, A Novel and Efficient Preparation of 2',3'–Dideoxynucleosides. Synthetic Communications, 15(5):401–409.

Rozenbaum et al., 1985, Antimoniotungstate (HPA23) Treatment of Three Patients With AIDS and One With Prodrome. Lancet i:450–451.

Sandstrom et al., 1985, Inhibition of Human T–cell Lymphotropic Virus Type III in Vitro By Phosphonoformate. Lancet i:1480–1482.

Sandstrom et al., 1987, Antiviral Therapy in AIDS Clinical Pharmacological Properties and Therapeutic Experience to Date. Drugs, 34:372–390.

Stoeckler et al., 1980, Human Erythrocytic Purine Nucleoside Phosphorylase: Reaction with Sugar–Modified Nucleoside Substrates, Biochemistry, 19:102–107.

Waqar et al., 1984, Effects of 2',3'-Dideoxynucleosides on Mammalian Cells and Viruses, J. Cellular Physiol., 121:402–408.

Yarchoan et al., 1987, Strategies For the Pharmacological Intervention Against HTLV–III/LAV. Ch. 19 AIDS: Modern Concepts and Therapeutic Challenges, Broder (Eds.), 335–360.

Lehninger, Albert L. Biochemistry, Second Edition, Worth Publishers, Inc., 1975, pp. 741, 184, and 218.

*Primary Examiner*—Gary L. Kunz
*Attorney, Agent, or Firm*—Pennie & Edmonds

[57] ABSTRACT

A method for inhibiting intracellular replication of HIV in an HIV-infected individual comprising contacting the HIV reverse transcriptase in the HIV-infected cells with 2',3'-dideoxyadenosine-5'-triphosphate whose source is 2',3'-dideoxyadenosine or a pharmaceutically acceptable salt or prodrug thereof.

4 Claims, 4 Drawing Sheets

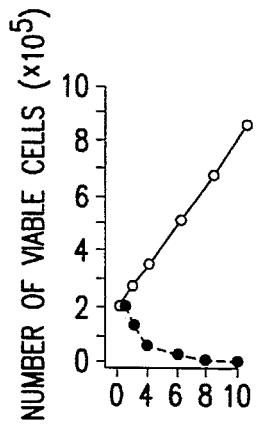 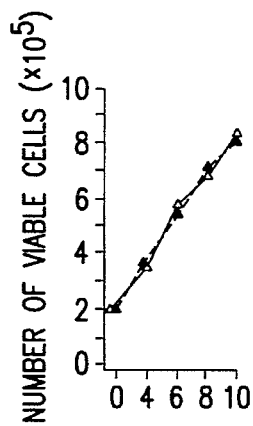 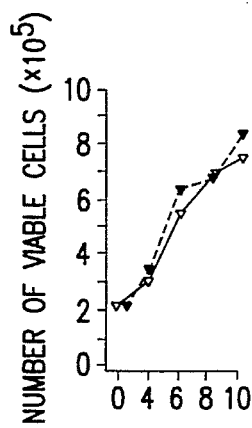 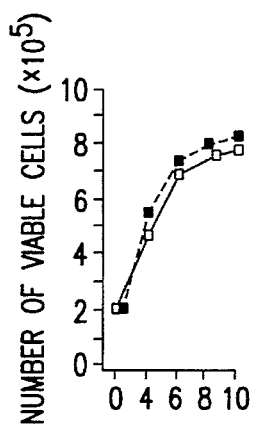
FIG.1a  FIG.1b  FIG.1c  FIG.1d
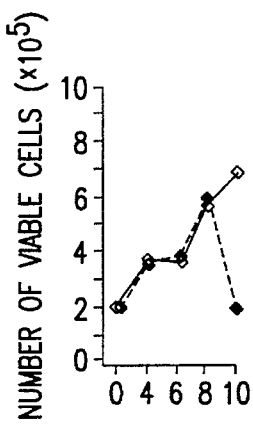
FIG.1e
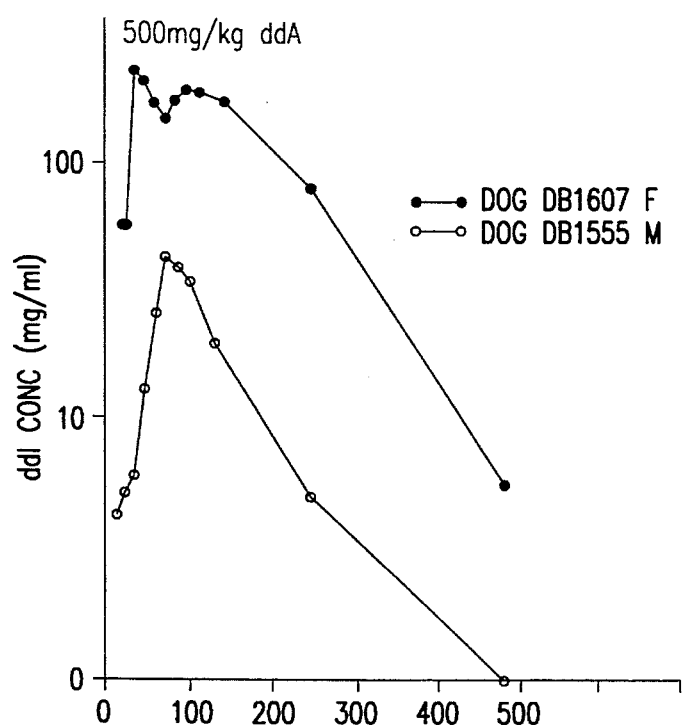
FIG.3

METHOD OF INHIBITING HIV REPLICATION WITH 2',3'-DIDEOXYADENOSINE

This application is a division of Ser. No. 07/663,288, filed Feb. 28, 1991, now U.S. Pat. No. 5,254,539; which is a continuation of Ser. No. 07/420,664, filed Aug. 28, 1989, abandoned; which is a continuation of Ser. No. 07/084,055, filed Aug. 11, 1987, now U.S. Pat. No. 4,861,759; which is a continuation-in-part of application Ser. No. 06/937,925, filed Dec. 4, 1986, abandoned; which is a continuation-in-part of application Ser. No. 06/769,016, filed Aug. 26, 1985, abandoned, each of which is incorporated by reference in its entirety.

The present invention relates to a method of treatment to prevent cytopathic effects of viruses. Of particular concern is protection against the cytopathic effects of HTLV/LAV virus (now known as human immunodeficiency virus (HIV)), the causative agent of acquired immune disease syndrome (AIDS), and its related disorders. Both parenteral use and oral use are described.

BACKGROUND OF THE INVENTION

The HIV virus which causes AIDS exerts a profound cytopathic effect on the helper/inducer T-cells, devastating the function of the immune system. The virus also shows a propensity to infect the brain with resulting neurological deterioration. The disease results in progressive debilitation and death.

While several antiviral agents have been tested for use as a treatment of AIDS patients, no fully satisfactory antiviral agent has been found. See, for example:

Mitsuya, H. et al. *Science*,226, 172–174 (1984) Broder, S. AIDS: *Modern Concepts and Therapeutic Challenges*. Marcel Dekker, Inc., New York 1987 Rosenbaum, W. et al. *Lancet*, i, 450–451 (1985) McCormick, J. B., Getchell, J. P., Mitchell, S. W., & Hicks, D. R. *Lancet*, ii, 1367–1369 (1984) Ho, D. D. et al. *Lancet*, i, 602–604 (1985) Sandstrom, E. G., Kaplan, J. C., Byington, R. E., & Hirsch, M. S. *Lancet*, i, 1480–1482 (1985)

Azidothymidine (AZT) is presently being used for treatment, but the serious toxic side reactions, and high cost of therapy present serious challenges in continued use for many patients.

SUMMARY OF THE INVENTION

It is an object of the invention to provide therapeutic compositions and methods of treatment which overcome the deficiencies of the prior art compositions and methods of treatment cited above.

It is, furthermore, the object of the present invention to provide compositions and methods of treatment which may be useful in treating patients with viral infections, particularly for treatment of AIDS patients.

It is a further object of the invention to provide means for intracellular delivery of the phosphorylated nucleosides to infected cells.

While the exact mechanism of antiviral activity of the compositions of the present invention is unknown, the probable mechanism involves modifying the naturally occurring 3'-carbon of the deoxyribose (of the viral RNA) so that it is not possible to form 5'--3' phosphodiester linkages necessary for DNA elongation in the replication of the virus from an RNA form to a DNA form. Once the drug enters a cell it is converted to a triphosphate The 2',3'-dideoxynucleoside purines which have been converted to triphosphates by cellular enzymes, are used in transcription instead of 2'-deoxynucleoside-5'-triphosphate. The 2',3'-dideoxynucleoside triphosphates act as DNA chain terminators, thus inhibiting DNA synthesis mediated by HIV reverse transcriptase and/or it can act by competitively inhibiting the binding of the natural substrate for reverse transcriptase.

One embodiment of the present invention involves the direct delivery of the triphosphate derivative to the host cells. It is well known by practitioners in the art that "unshielded" triphosphates cannot be used as drugs because triphosphate compounds do not penetrate cell membranes. Accordingly, the triphosphate derivatives of this invention may be delivered by means of liposomes, small particles (about 25 uM to 1 uM in diameter) which serve as intracellular transport systems to deliver normally nonabsorbable drugs across the cell membrane. The use of liposomes for drug delivery is well known in the art and is based on a phopholipid's ability to spontaneously form bilayers in aqueous environments. One method of forming liposomes is by agitating phospholipids in aqueous suspensions at high frequencies; this results in the closed vesicles characteristic of liposomes. Once inside the cells, the triphosphate derivatives act, as noted above, in the suppression of the cytopathic effects of HIV. The use of a liposome delivery system is clearly indicated as particularly appropriate based on our data indicating the triphosphate form is the drug that is active inside the cell.

In the specification and claims a so-called "safe" use is noted and is defined as the use of a treating agent in a concentration sufficient to suppress viral replication, but lower than the concentration which will harm the host cell.

MATERIAL INFORMATION DISCLOSURE

Furmanski et al., "Inhibition by 2',3'-Dideoxythymidine of Retroviral Infection of Mouse and Human Cells," *Cancer Letters*, 8:307–315, 1980.

Waqar et al., "Effects of 2',3'-Dideoxynucleosides on Mammalian Cells and Viruses, "*Journal of Cellular Physiology*, 121:402–408 (1984).

SPECIFIC DESCRIPTION OF THE INVENTION

Active Ingredient:

The compositions of the present invention comprise purine nucleosides with the ribose moiety of the molecule in the 2',3'-dideoxy configuration, and a pharmaceutically acceptable carrier. In the preferred embodiment, the active ingredient is 2',3'-dideoxyinosine, 2',3'-dideoxyguanosine, or 2',3'-dideoxyadenosine, illustrated below:

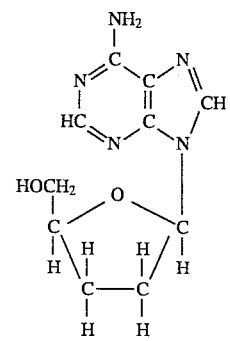

-continued
dideoxyadenosine

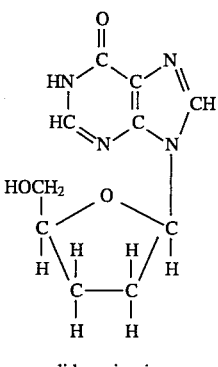

dideoxyinosine

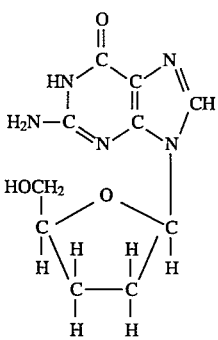

dideoxyguanosine

Preferred esters of the compounds of the formulas include carboxylic acid esters in which the non-carbonyl moiety of the ester grouping is selected from straight or branched chain alkyl, alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); sulphonate esters such as alkyl- or aralkylsulphonyl (e.g., methanesulphonyl); and mono-, di- or tri-phosphate esters.

Any reference to the above-described compounds also includes a reference to a pharmaceutically acceptable salt thereof with regard to the above-cited derivatives. Unless otherwise specified, any alkyl moiety present advantageously contains 1 to 18 carbon atoms, particularly 1 to 4 carbon atoms. Any aryl moiety present in such esters advantageously comprises a phenyl group, including a substituted phenyl group.

Examples of pharmaceutically acceptable salts of the compounds of formula (1) and pharmaceutically acceptable derivatives thereof include base salts, e.g., derived from an appropriate base, such as alkali metal (e.g., sodium), alkaline earth metal (e.g., magnesium) salts, ammonium and $NX_4$ (wherein X is $C_{1-4}$ alkyl). Physiologically acceptable salts containing a hydrogen atom or an amino group include salts of organic carboxylic acids such as acetic, lactic, tartaric, malic, isothionic, lactobionic and succinic acids; organic sulfonic acids such as methanesulfonic, ethanesulfonic, benzenasulfonic and p-tolunesulfonic acids and inorganic acids such as hydrochloric, sulfuric, phosphoric and sulfamic acids. Physiologically acceptable salts of a compound containing any hydroxy group include the anion of said compound in combination with a suitable cation such as $Na^+$, $NHY^+_4$, and $NX_4^+$ (wherein X is a $C_{1-4}$ alkyl group).

Specific examples of pharmaceutically acceptable derivatives of the compound of the formulas that may be used in accordance with the present invention include the monosodium salt and the following 5' esters: monophosphate; disodium monophosphate; diphosphate; triphosphate; acetate; 3-methyl-butyrate; octanoate; palmitate; 3-chloro benzoate; benzoate; 4-methyl benzoate; hydrogen succinate; pivalate; and mesylate.

Also included within the scope of this invention are the pharmaceutically acceptable salts, esters, salts of such esters, nitrile oxides, or any other covalently linked or non-linked compound which, upon administration to the recipient, is capable of providing (directly or indirectly) a nucleoside analog as described above, or an anti-virally active metabolite or residue thereof. All of these compounds are active and relatively non-toxic at concentrations of sufficient potency for effective inhibition of viral infectivity and replication.

Pharmaceutically Acceptable Carrier:

It is possible for the nucleoside of the present invention to be administered alone in solution. However, in the preferred embodiment, the active ingredient(s) may be used or administered in a pharmaceutical formulation. These formulations comprise at least one active ingredient (the nucleoside), together with one or more pharmaceutically acceptable carriers and/or other therapeutic agents. As included within the scope of this invention, "acceptable" is defined as being compatible with other ingredients of the formulation and non-injurious to the patient or host cell. These carriers include those well known to practitioners in the art as suitable for oral, rectal, nasal, topical, buccal, sublingual, vaginal, or parenteral (including subcutaneous, intramuscular, intravenous, and intradermal) administration. Specific carriers suitable for use in the invention are further defined below.

In general, a suitable dose is in the range of 1.0 to 120 mg per kilogram body weight per day and most preferably in the range 10 to 60 mg per kilogram body weight per day. The desired dose is provided in several increments at regular intervals throughout the day by continuous infusion or sustained release formulations. The doses will need to be modified according to the patient's hepatic, renal, and bone marrow function, functions which are frequently abnormal in patients with advanced retroviral infections.

Ideally, the active ingredient is administered to achieve peak plasma concentrations of the active compound of from about 0.5 uM to about 50 uM, and preferably about 1 to 30 uM. This may be achieved, for example, by the intravenous injection of 0.1% to 50% concentration in solution of the active ingredient or may be administered orally in doses of about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient. Ideally, concentrations in the cerebrospinal fluid should reach 10–100% of the circulating plasma concentrations. This may be achieved by systemic or intrathecal administration.

The 2',3'-dideoxynucleosides may be administered orally in liquid or in tablet form, and may include one or more of the following: lactose (hydrous, fast flow), microcrystalline cellulose, colloidal silicon dioxide, croscarmellose sodium, magnesium stearate, stearic acid, and other excipients, colorants, and pharmacologically compatible carriers. Compositions for oral use may be administered to patients in fasting and non-fasting states.

Formulations of the present invention suitable for oral administration (including sustained release formulations) may be presented as discrete units such as capsules, cachets or tablets, each containing a predetermined amount of the active ingredient; as a powder or granules; as a solution or a suspension in an aqueous liquid; in an oil-in-water liquid emulsion or a water-in-oil liquid emulsion. The active ingredient may also be presented as a bolus, electuary or paste.

Tablets may optionally be provided with an enteric coating, to provide release in parts of the gut other than the stomach.

Formulations suitable for topical administration in the mouth include lozenges comprising the active ingredient in a flavor, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams, or spray formulas containing in addition to the active ingredient such carriers as are known in the art to be appropriate.

Formulations suitable for parenteral administration include aqueous and non-aqueous, isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

As previously indicated, it is highly desirable to administer medications by oral route when long-term treatment is required. Since the instantly claimed compounds are not stable within the acid range, it is necessary, in order to provide acceptable bioavailability, to buffer the compositions to obtain a composition in the neutral (pH 6–pH 8) range. At about pH 7 the bioavailability increases greatly so that oral administration of the nucleosides becomes practicable.

The antiviral agents of the invention may be used in conjunction with other antiviral drugs or antibiotics. Immune modulating therapy including bone marrow or lymphocyte transplants may be used concurrently.

DETAILED DESCRIPTION OF THE DRAWINGS

Figure 2A:
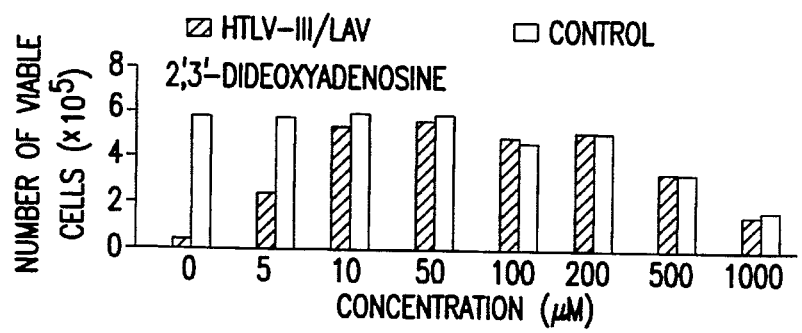
Figure 2B:
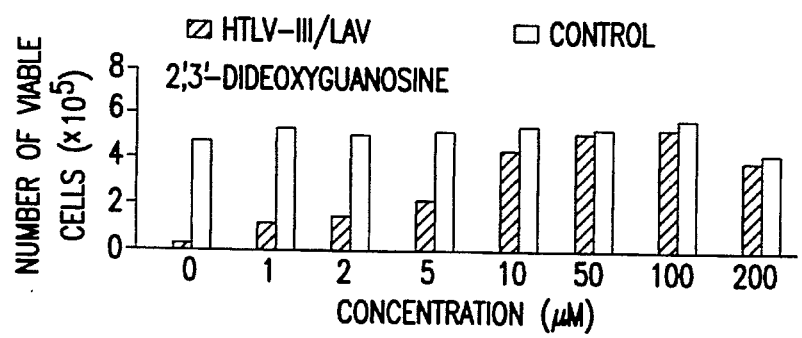
Figure 2C:
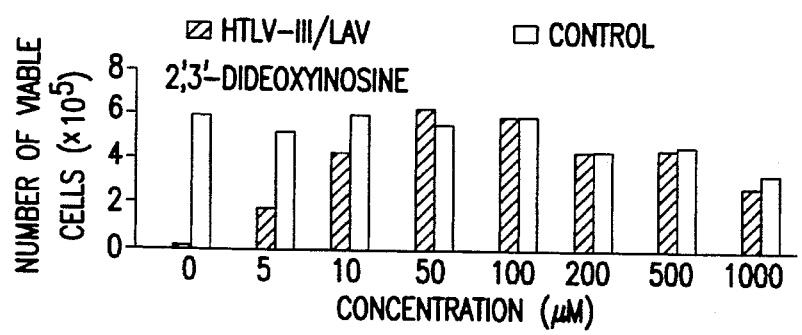
Figure 2D:
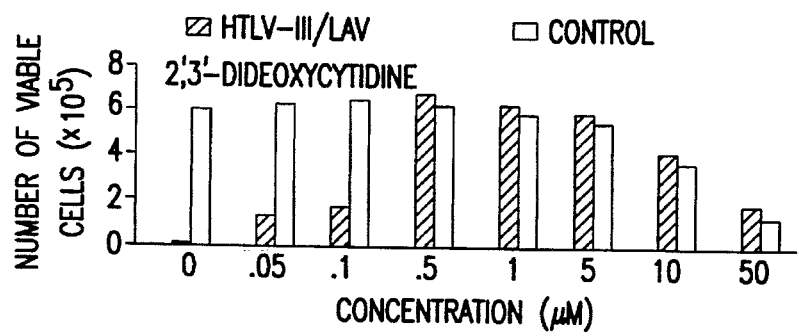
Figure 2E:
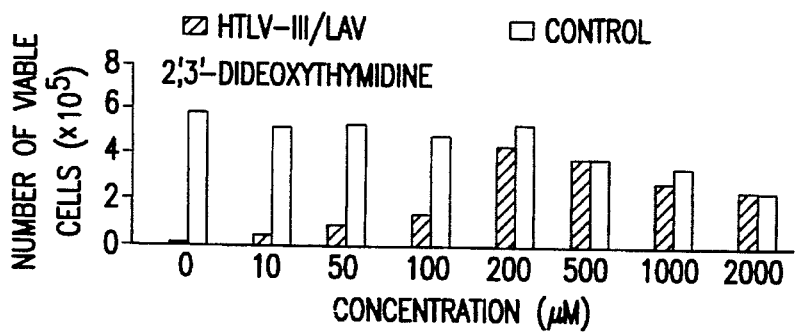
Figure 2F:
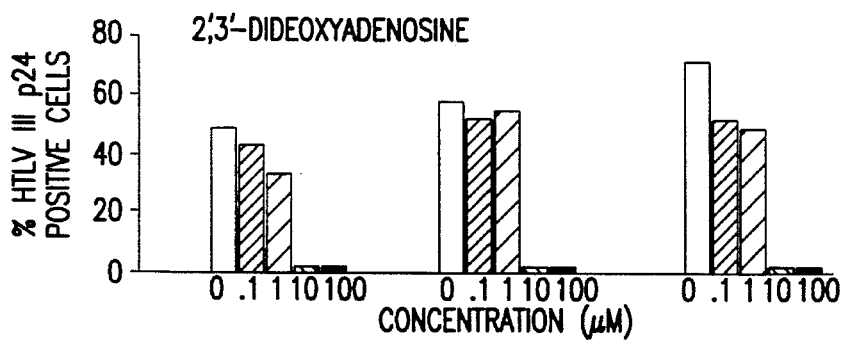
Figure 2G:
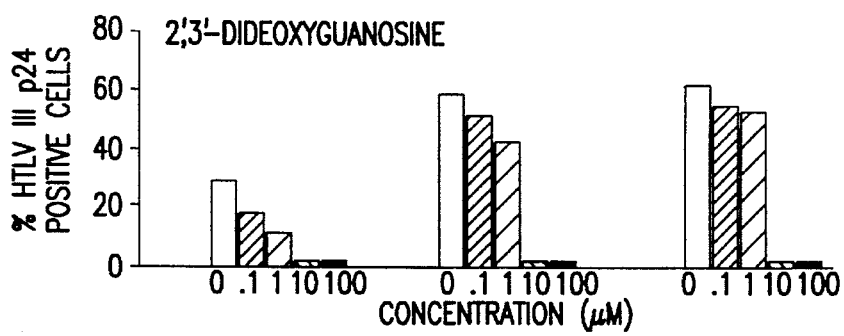
Figure 2H:
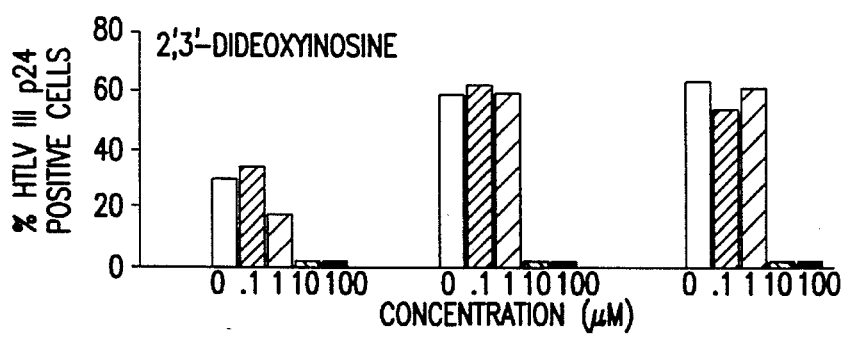
Figure 2I:
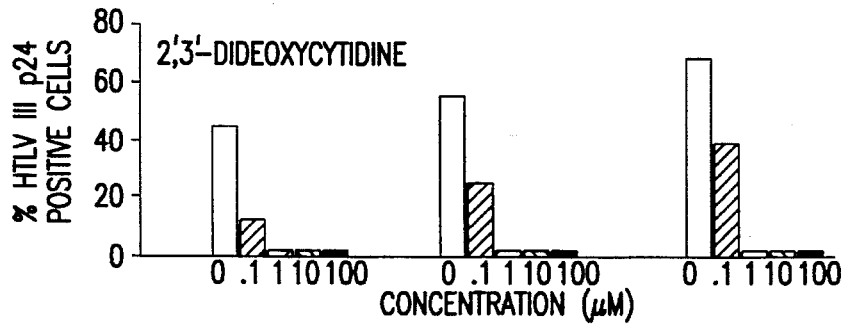

FIGS. 1a–1e, which shows the survival and growth of human ATH8 cells in the presence of 2',3'-dideoxynucleosides when exposed to HIV (HTLV-III/LAV), $2 \times 10^5$ ATH8 cells were treated with polybrene, exposed to HTLV-III$_B$ (2,000 virus particles/cell), resuspended in culture tubes, and cultured (solid symbols) in the absence of drugs (FIG. 1a); or in the presence of 50 uM 2',3'-dideoxyadenosine (Calbiochem-Behring Corp., LaJolla, Calif.) (FIG. 1b); in the presence of 50 uM 2',3'-dideoxyinosine (Calbiochem-Behring Corp.) (FIG. 1c); in the presence of 1 uM 2',3'-dideoxycytidine (Calbiochem-Behring Corp.) (FIG. 1d); and in the presence of 500 uM 2',3'-dideoxythymidine (P.L. Biochemicals Inc., Milwaukee, Wis.) (FIG. 1e). Control cells were similarly treated but were not exposed to the virus (open symbols). At various time points, total viable cells were counted as described in Example 1.

In FIGS. 2a–2e, which show the inhibition of cytopathic effect of HIV (HTLV-III/LAV) by various 2,'3'-dideoxynucleosides against target ATH8 cells, $2 \times 10^5$ ATH8 cells were preexposed to polybrene, exposed to HTLV-III$_B$ (2,000 virus particles/cell) in culture tubes (solid columns) in the presence or absence or various concentrations of 2',3'-dideoxyadenosine, 2',3'-didoxyinosine, 2',3'-dideoxyguanosine (P.L. Biochemicals Inc.), 2',3'-dideoxycytidine, or 2',3'-dideoxythymidine. Control cells (open columns) were similarly treated but were not exposed to the virus. On day 5, total viable cells were counted as described in Example 1.

In FIGS. 2b–2j, which show the inhibition of the infectivity and replication of HIV (HTLV-III/LAV) in H9 cells by various 2',3'-dideoxynucleosides, $10^5$ H9 cells were exposed to various concentrations of 2',3'-dideoxynucleosides for 4 hours, then to 2 ug/ml polybrene for 30 minutes, pelleted, and exposed to HTLV-III$_B$ (3,000 virus particles/cell) for 1.5 hours. Cells were resuspended in fresh complete medium and cultured in tubes at 37° C. in 5% $CO_2$-containing humidified air. The cells were continuously exposed to 2',3'-dideoxynucleosides. On days 8 (left), 9 (middle), and 10 (right) in culture, the percentage of the target H9 cells expressing p24 gag protein of HIV (HTLV-III/LAV) was determined by indirect immunofluorescence microscopy by using anti-HIV p24 murine monoclonal antibody (M26 provided by Drs. F. D. Veronese and R. C. Gallo).

In FIGS. 2k–2o, which shows protection (or lack of protection) of ATH8 cells by various adenosine congeners against the cytopathic effect of HIV (HTLV-III/LAV), $2 \times 10^5$ ATH8 cells were preexposed to polybrene, exposed to HTLV-III$_B$ (2,000 virus particles/cell,), resuspended in culture tubes (solid columns) in the presence or absence of various amounts of adenosine congeners: 2',3'-dideoxyadenosine (FIG. 2k); 2'-deoxyadenosine (Calbiochem-Behring Corp.) (FIG. 2l); 3'-deoxyadenosine (cordycepin; Behringer-Manheim GmbH, West Germany) (FIG. 2m); adenosine arabinoside (d); and 2',3',5'-trideoxydenosine (FIG. 2n) (both provided by Drs. D. Johns, J. Driscoll, and G. Milne). The primed numbers in (FIG. 2l) refer to positions in the sugar moiety. Control cells (open columns) were not exposed to the virus. On day 5, the total viable cells were counted as described in Example 1.

FIG. 3 shows ddI concentration in the plasma of beagle dogs up to 500 minutes after oral administration of ddA.

Specific Description of the Process

In the system, HIV (HTLV-III/LAV) (as cell-free virus) exerts a profound cytopathic effect on the target T-cells by day 4 in culture, and by day 10, >98% of cells are killed by the virus (FIG. 1-a). The killing of cells can be monitored quantitatively as a function of the starting dose of virus (Table 1). When ATH8 cells are used in a 7-day assay, 5 virus particles/cell represented the minimum cytopathic dose of virus. In the experiments reported below, 2,000 or 3,000 virus particles/cell were used in order to test various compounds under conditions of substantial virus excess.

FIGS. 2a–2e (b–e) and FIG. 2-a illustrate the protective effect of 2',3'-dideoxynucleosides on the survival and growth of ATH8 cells when exposed to HIV (HTLV-III/LAV). In the present experimental conditions, 2',3'-dideoxythymidine required relatively high concentrations to exert a protective effect, and unlike the other comparable dideoxynucleosides tested, its capacity to nullify the cytopathic effect of the virus was lost on day 10 of the culture (FIG. 1–3 and FIG. 2e). It is not possible to deduce which compounds will work against HIV and be non-toxic for human cells from first principles or the prior art.

Figure 2J:
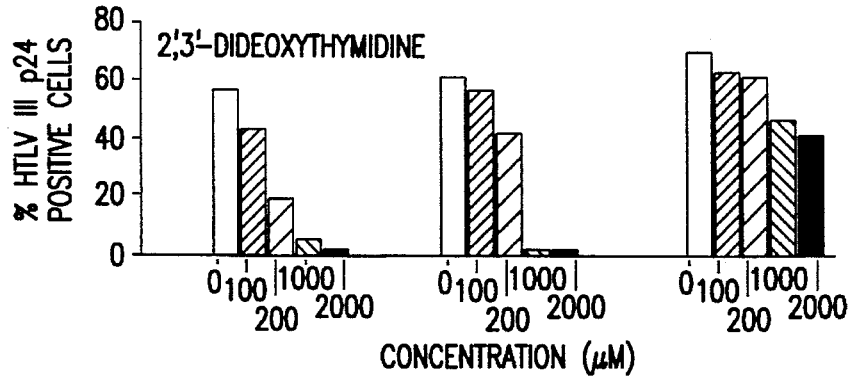
Figure 2K:
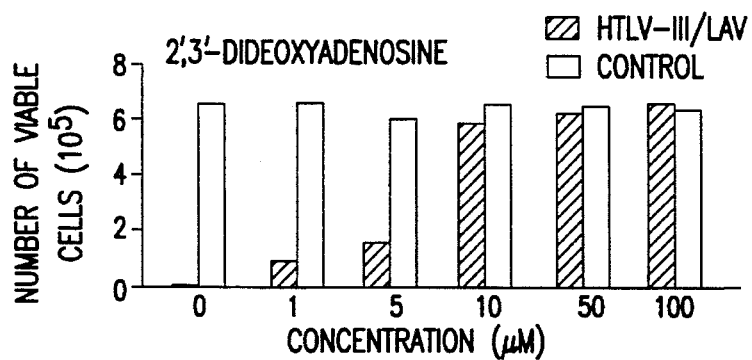
Figure 2L:
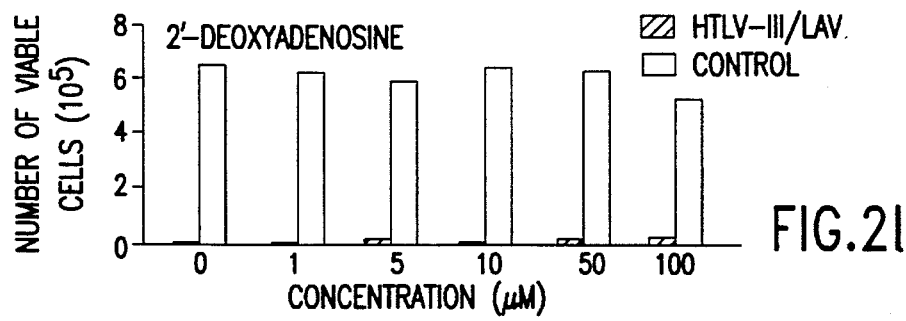
Figure 2M:
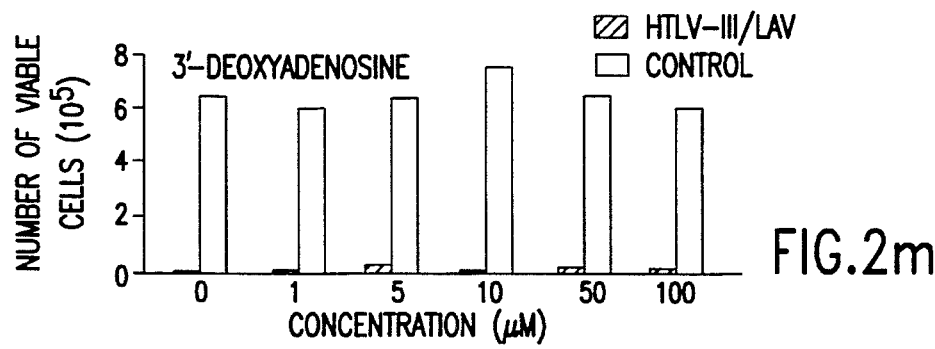
Figure 2N:
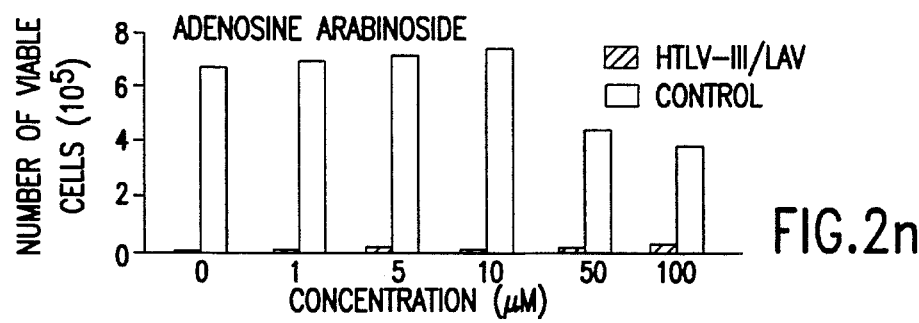
Figure 2O:
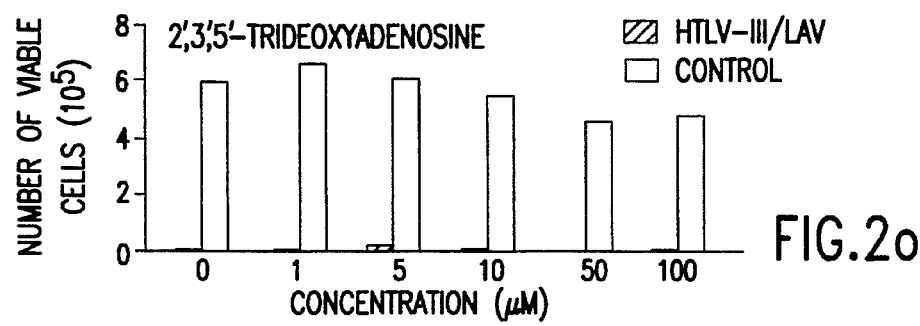

These anti-viral effects were confirmed in a different system, using the expression of the HIV (HTLV-III/LAV) p 24 gag protein in H9 cells (FIGS. 2f–2j). The H9 cells are relatively resistant to the cytopathic effect of HIV (HTLV-III/LAV), and p24 gag protein expression following exposure to virions may be used as an index of viral infectivity and replication in vitro. Again, 2',3'-dideoxythymidine required relatively higher concentrations to mediate an antiviral effect, and this compound allowed a resumption of viral replication by day 10 of culture (FIG. 2j, bottom). Each drug must, therefore, be evaluated in its own right.

There was tested the effects of the various 2',3'-dideoxynucleosides on the antigen-specific and lectin-induced reactivity of normal lymphocytes in vitro (Table 2). There was used a normal clone (TM3) of tetanus-toxoid specific helper/inducer T-cells to monitor the effects of the compounds on antigen-driven activation and normal circulating lymphocytes to monitor effects on pokeweed mitogen and phytohaemagglutinin-driven activation. Concentrations of these compounds, including those that were 10- to 20-fold higher than those necessary to block the in vitro infectivity and cytopathic effect of HIV (HTLV-III/LAV) left the in vitro immune reactivity of normal lymphocytes basically intact.

The mechanisms by which 2',3'-dideoxynucleosides suppress the replication of HIV (HTLV-III/LAV) are not fully known. It is known that the 5'-triphosphate product of 2',3'-dideoxyadenosine, -dideoxyguanosine, and -dideoxyadenosine can inhibit cellular DNA polymerases beta and gamma, as well as viral reverse transcriptase (vide infra), but not mammalian DNA polymerase alpha. DNA polymerase alpha is assumed to be the key DNA synthetic enzyme for DNA replication during cell division, and it also has a role in DNA repair. Of interest, Herpes simplex type I DNA polymerase is reported to be as resistant to 2',3'-dideoxythymidine as cellular DNA polymerase alpha. Unphosphorylated dideoxynucleosides have rather negligible effects on the growth of cultured mammalian cells (a phenomenon which is confirmed here in human T-cells). This is believed to be so because of comparatively inefficient intracellular conversion to the corresponding 5'-triphosphates coupled with the resistance of DNA polymerase alpha to low levels of the 5'-triphosphates.

EXAMPLE 1

With reference to Table 1, a human tetanus toxoid-specific T-cell line, established by repeated cycles of stimulation with antigen as described in Mitsuya et al., *Science*, 225:1484–1486 (1984), was cloned in the presence of lethally irradiated (12,000 rad) human T-lymphotropic virus type I (HTLV-I)-producing MJ-tumor cells in 96-well microtiter culture plates (Costar, Cambridge, Mass.). Clone ATH8 (obtained from a culture plated at 0.5 cells per well) was selected for drug screening on the basis of its rapid growth (in the presence of interleukin-2) and exquisite sensitivity in vitro to the cytopathic effect of HIV (HTLV-III/LAV). ATH8 clone bears several distinct copies of HTLV-I in its genome when assessed by Southern blot hybridization using a radiolabelled HTLV-I cDNA probe but does not produce detectable amounts of HTLV-I p24 gag protein. $10^5$ ATH8 cells were pre-exposed to 2 ug/ml polybrene for 30 minutes, pelleted, exposed to various amounts of HTLV-III$_B$, resuspended in 2 ml complete medium (RPMI supplemented with 15% undialysed, heat-inactivated fetal calf serum, 4 mM L-glutamine, $5\times10^{-5}$ 2-mercaptoethanol, 50 U/ml penicillin, and 50 ug/ml streptomycin) containing 15% (vol/vol)-interleukin 2 (lectin-depleted; Cellular Products Inc., Buffalo, N.Y.), and incubated in culture tubes (3033, Falcon, Oxnard, Calif.) at 37° C. in 5% $CO_2$-containing humidified air. On day 7, the total viable cells were counted by the trypan blue dye exclusion method. Table 1 shows the cytopathic effect of HIV (HTLV-III/LAV) on the ATH8 cells; data are expressed as the arithmetic means ±1 standard deviation for duplicate determinations.

TABLE 1

| Cytopathic Effect of HTLV-III/LAV on ATH8 Cells | |
| --- | --- |
| Number of HTLV-III$_B$ Virus Particles/Cell | Number of Viable ATH8 Cells (×$10^5$) |
| 0 | 3.37 ± 0.1 |
| 0.05 | 3.36 ± 0.04 |
| 0.5 | 3.26 ± 0.15 |
| 5 | 1.97 ± 0.2 |
| 50 | 1.78 ± 0.16 |
| 500 | 0.37 ± 0.02 |
| 5,000 | 0.30 ± 0.01 |

TABLE 2

| | Effect of 2',3'-Dideoxynucleosides on the in vitro Immune Reactivity of Normal Lymphocytes | | | | | | | | | | | |
| --- | --- | --- | --- | --- | --- | --- | --- | --- | --- | --- | --- | --- |
| Responder | | Adenosine[1] | | Guanosine[1] | | Inosine[1] | | | Cytidine[4] | | Thymidine[4] | |
| Cells | None | 10 | 100 | 10 | 100 | 10 | 100 | None[4] | 1 | 10 | 200 | 2,000 |
| Clone TM3[2] | 75 ± 6 | 86 ± 8 | 67 ± 2 | 66 ± 5 | 77 ± 1 | 62 ± 4 | 81 ± 4 | 12 ± 1 | 13 ± 1 | 8 ± 1 | 9 ± 1 | 9 ± 1 |
| PBM + PHA[3] | 310 ± 39 | 289 ± 18 | 314 ± 37 | 350 ± 4 | 469 ± 9 | 298 ± 20 | 355 ± 37 | 82 ± 1 | 101 ± 1 | 86 ± 3 | 86 ± 6 | 77 ± 8 |
| PBM + PWM[3] | 63 ± 2 | 63 ± 5 | 57 ± 3 | 73 ± 8 | 62 ± 5 | 61 ± 1 | 62 ± 5 | 24 ± 1 | 23 ± 3 | 15 ± 3 | 31 ± 1 | 31 ± 1 |

[1]All nucleosides tested ar of 2',3'-dideoxy-configuration. Concentrations (uM) of each 2',3'-dideoxynucleoside bring about virtually complete inhibition of the cytopathic effect of HTLV-III/LAV (FIGS. 1 and 2-a) and the viral p24 expression (except 2',3'-dideoxythymidine; see FIG. 2-b). [3]$^3$H-thymidine incorporation was used as an indicator of activation of responder cells (vide infra), unless otherwise indicated.
[2]$5 \times 10^4$ normal helper/inducer TM3 cells were stimulated with tetanus toxoid (0.6 limiting flocculation units/ml) plus $10^5$ irradiated (4,000 rad) autologous peripheral blood mononuclear cells (PBM) as a source of accessory cells and cultured for 72 hours in the presence or absence of the 2',3'-dideoxynucleoside. After exposure to 0.5 uCi$^3$H-thymidine or 1 uCi $^3$H-uidine for the final 5 hours, cells were harvested onto glass fibers and the incorporated radioactivity was counted. Data are expressed as the arithmetic mean counts per minute (×$10^3$) ± 1 standard deviation triplicate determinations.
[3]$10^6$ PBM from a healthy individual were stimulated with phytohaemagglutinin (PHA) or pokeweed mitogen (PWM) and cultured 72 hours and treated as described above.
[4]$^3$H-uridine incorporation was used as an indicator of activation of the responder cells.

EXAMPLE 2

Beagle dogs were administered 500 mg/kg bodyweight of 2',3'-dideoxyadenosine (ddA) as either a short (15 minutes) intravenous infusion in saline, or as an oral gavage in 0.1N acetate buffer (ph 7.0). Drug concentration in both solutions was 25 mg/ml, which necessitated the administration of about 300 ml of solution by either route. Oral bioavailability was calculated for dideoxyinosine (the plasma product of dideoxyadenosine) based on the ddA dose. Oral bioavailability was calculated to be 41.6% with the orally administered ddA was converted almost entirely to 2',3'-dideoxyinosine (ddI). Both ddA and ddI have anti-retroviral activity against HIV. FIG. 3 shows ddI concentration up to 500 minutes after oral administration of ddA.

EXAMPLE 3

The antiviral activity of the dideoxynucleosides of the present invention against a variety of viruses were compared. The results, shown in Table 3, indicate that the compositions of the present invention are selectively effective against HIV virus.

TABLE 3

Antiviral Activity of 2',3'-Dideoxynucleosides

Minimal Inhibitory Concentration (uM)[1]

| Virus | | Dideoxy-uridine | Dideoxy-thymidine | Dideoxy-adenosine | Dideoxy-cytidine |
|---|---|---|---|---|---|
| DNA virus | HSV-1[2] | >2,000[6] | >2,000 | >2,000 | >2,000 |
| | HSV-1[2] | >2,000 | >2,000 | >2,000 | >2,000 |
| | Vaccinia[2] | >2,000 | >2,000 | >2,000 | >2,000 |
| RNA virus | Vesicular Stomatitis Virus[2,3] | >2,000 | >2,000 | >2,000 | >2,000 |
| | Reovirus-1[4] | >2,000 | >2,000 | >2,000 | >2,000 |
| | Sindbis Virus[4] | >2,000 | >2,000 | >2,000 | >2,000 |
| | Coxsackie Virus B4[3] | >2,000 | >2,000 | >2,000 | >2,000 |
| | Semliki Forest Virus[4] | >2,000 | >2,000 | >2,000 | >2,000 |
| | Parainfluenza Virus-3[4] | >2,000 | >2,000 | >2,000 | >2,000 |
| | Polio Virus-1[3] | >2,000 | >2,000 | >2,000 | >2,000 |
| Retrovirus | HTLV-III[5] | >100 | 200 | 5 | 0.3 |

[1]Required to reduce virus-induced cytopathogenicity by 50%.
[2]Antiviral activity measured in primary rabbit kidney cell cultures.
[3]Antiviral activity measured in Hela cell cultures.
[4]Antiviral activity measured in Vero cell cultures.
[5]Antiviral activity measured in T4+ human T cell (ATH8) cultures.
[6]A value >2,000 denotes that at concentrations of up to 2,000 uM the nucleoside failed to inhibit the specified virus.
Note:
2',3'-dideoxyadenosine and 2',3'-dideoxycytidine were not active against the broad spectrum of DNA and RNA viruses shown above, except that they were active against HIV the human HTLV-III (AIDS-causing) virus.

What is claimed is:

1. A method for inhibiting HIV replication within an HIV-infected cell comprising contacting the HIV reverse transcriptase within that cell with 2',3'-dideoxyadenosine-5'-triphosphate.

2. A method for the intracellular inhibition of HIV replication in an HIV-infected individual comprising contacting the HIV reverse transcriptase in the HIV-infected cells of that individual with 2',3'-dideoxyadenosine-5'-triphosphate.

3. The method of claim 2, wherein the source of the 2',3'-dideoxyadenosine-5'-triphosphate is 2',3'-dideoxyadenosine or a pharmaceutically acceptable salt or prodrug ester thereof which is administered in a therapeutically effective amount to the individual.

4. A method for inhibiting HIV replication within an HIV-infected cell comprising treating said cells with 2',3'-dideoxyadenosine or a pharmaceutically acceptable salt thereof, wherein the resulting 2',3'-dideoxyadenosine-5'-triphosphate contacts the intracellular HIV reverse transcriptase.

* * * * *